United States Patent
Matsunaga et al.

(10) Patent No.: US 7,842,101 B2
(45) Date of Patent: Nov. 30, 2010

(54) OXIDATIVE HAIR DYE COMPOSITION

(75) Inventors: Kenichi Matsunaga, Sumida-ku (JP); Hajime Miyabe, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/602,300

(22) PCT Filed: May 30, 2008

(86) PCT No.: PCT/JP2008/001381

§ 371 (c)(1),
(2), (4) Date: Nov. 30, 2009

(87) PCT Pub. No.: WO2008/149535

PCT Pub. Date: Dec. 11, 2008

(65) Prior Publication Data

US 2010/0154135 A1 Jun. 24, 2010

(30) Foreign Application Priority Data

May 31, 2007 (JP) .............................. 2007-146275

(51) Int. Cl.
*A61Q 5/10* (2006.01)
(52) U.S. Cl. ....................... 8/405; 8/406; 8/435; 8/552; 8/554; 8/606
(58) Field of Classification Search .................. 8/405, 8/406, 435, 552, 554, 606
See application file for complete search history.

(56) References Cited

U.S. PATENT DOCUMENTS

| 5,476,649 | A | | 12/1995 | Naito et al. |
| 5,587,155 | A | * | 12/1996 | Ochiai et al. ............. 424/70.28 |
| 2001/0036448 | A1 | | 11/2001 | Pereira et al. |
| 2003/0202954 | A1 | | 10/2003 | Pereira et al. |
| 2005/0123498 | A1 | | 6/2005 | Pereira et al. |

FOREIGN PATENT DOCUMENTS

| EP | 0 483 689 | 5/1992 |
| JP | 63 316712 | 12/1988 |
| JP | 4 164014 | 6/1992 |
| JP | 4 173719 | 6/1992 |
| JP | 4 230614 | 8/1992 |
| JP | 6 87724 | 3/1994 |
| JP | 9 143135 | 6/1997 |
| JP | 2001 213739 | 8/2001 |
| JP | 2003 528125 | 9/2003 |
| JP | 2005 206524 | 8/2005 |
| JP | 2007 15986 | 1/2007 |

OTHER PUBLICATIONS

U.S. Appl. No. 12/602,171, filed Nov. 30, 2009, Matsunaga, et al.

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

Provided is an oxidative hair dye composition containing components (A) an iso-fatty acid or an anteiso-fatty acid having from 19 to 30 carbon atoms, or a salt thereof; (B) a polymer or a copolymer of a diallyl quaternary ammonium salt; (C) an oxidation dye and (D) an alkali agent.

6 Claims, No Drawings

OXIDATIVE HAIR DYE COMPOSITION

CROSS REFERENCE TO RELATED APPLICATION

This application is a 371 of PCT/JP08/001381, filed on May 30, 2008, and claims priority to Japanese Patent Application No. 2007-0146275, filed on May 31, 2007.

TECHNICAL FIELD

The present invention relates to an oxidative hair dye composition containing a specific branched fatty acid or salt thereof.

BACKGROUND OF THE INVENTION

Hair exposed to chemical treatments with a permanent waving solution, oxidation hair dye (for coloring), or hair bleaching agent (for bleaching) is damaged due to a partial loss of its component or structure. The damage of the hair caused by such chemical treatments tends to be severer by the heat of a drier, hair iron, or the like or physical stimulation resulting from daily hair care routine such as brushing. Chemical treatments such as permanent waving, hair coloring and hair bleaching are usually performed with intervals of several months. Due to physical stimulation during this period, there appears a large difference in the damage degree between a hair root portion which has grown after such a chemical treatment and a hair tip portion exposed thereto.

Application of an oxidation hair dye to the hair having two portions different in damage degree tends to cause uneven dyeing because the greatly damaged hair tip portion tends to be dyed deeply and the slightly damaged hair root portion is relatively poorly dyed. To overcome such a problem, there is a demand for the development of oxidation hair dyes capable of uniformly dyeing hair having portions different in damage degree.

Branched fatty acids are well known as raw materials for hair cosmetic compositions. Hair cosmetic compositions containing an iso-fatty acid (a branched fatty acid having a methyl group at the second carbon atom from the carbon atom at the end of the fatty acid chain) or an anteiso-fatty acid (a branched fatty acid having a methyl group at the third carbon atom from the carbon atom at the end of the fatty acid chain) are also known (Patent Documents 1 to 4). Fatty acids derived from lanolin contain such an iso-fatty acid or anteiso-fatty acid and hair cosmetic compositions containing such a lanolin fatty acid are also known (Patent Documents 5 and 6).

Patent Documents 1 to 3 give Examples of shampoos containing 18-methylicosanoic acid and cationic cellulose. Patent Document 4 gives Example of a hair bleaching agent containing a lanolin fatty acid and it describes that the agent can suppress hair damage and provide the hair with an excellent feel. Patent Document 6 also gives Examples of an oxidation hair dye and a hair bleaching agent, each containing a lanolin fatty acid.

It is however not known at all that addition of such a branched fatty acid and a cationic polymer in combination has an influence on dyeing properties of the resulting hair dye composition, in particular, an oxidative hair dye composition containing, as the branched fatty acid, an iso-fatty acid or anteiso-fatty acid having from 19 to 30 carbon atoms, or salt thereof together with a cationic polymer is excellent in uniform dyeing of hair having portions different in damage degree and also excellent in the durability of its effect (meaning that uniformity is kept even when the color of the hair fades out gradually by shampooing).

[Patent Document 1] EP-A-0483689
[Patent Document 2] JP-A-4-230614
[Patent Document 3] JP-A-6-87724
[Patent Document 4] JP-A-2005-206524
[Patent Document 5] JP-A-63-316712
[Patent Document 6] JP-A-2001-213739

DISCLOSURE OF THE INVENTION

The present invention provides an oxidative hair dye composition containing the following Components (A) to (D):

(A) an iso-fatty acid or an anteiso-fatty acid having from 19 to 30 carbon atoms, or a salt thereof,
(B) a polymer or a copolymer of a diallyl quaternary ammonium salt,
(C) an oxidation dye, and
(D) an alkali agent.

MODE FOR CARRYING OUT THE INVENTION

The present invention relates to an oxidative hair dye composition having good hair dyeing properties, particularly capable of dyeing hair uniformly and excellent in durability of its effect. The term "in the hair dye composition of the present invention" used herein with respect to the content of each component means "in the total composition composed of the first agent and the second agent" in the case of a two-part composition and "in the total composition composed of the first agent, the second agent, and the third agent" in the case of a three-part composition.

The present inventors have found that an oxidative hair dye is equipped with the above-described performances when it uses an iso-fatty acid or anteiso-fatty acid having from 19 to 30 carbon atoms, or salt thereof and a specific cationic polymer in combination.

The hair dye composition of the present invention is presumed to form a complex, which is firm and easily fixed to hair, between the fatty acid as Component (A) and the diallyl quaternary ammonium polymer having a cationic group as Component (B) under alkaline conditions. Due to this, the hair dye composition of the present invention prevents hair damage and exhibits excellent hair dyeing properties.

[(A): Iso-Fatty Acid or Anteiso-Fatty Acid, or Salt Thereof]

Component (A) to be used in the present invention is an iso-fatty acid having from 19 to 30 carbon atoms or an anteiso-fatty acid having from 19 to 30 carbon atoms, or a salt thereof. These fatty acids are preferably saturated fatty acids. From the standpoint of a hair damage preventing effect, a good dyeing effect such as uniform dyeing, and excellent durability of such effects, these fatty acids have preferably from 19 to 24 carbon atoms, more preferably from 19 to 22 carbon atoms.

Specific examples of the iso-fatty acid include 17-methyloctadecanoic acid, 18-methylnonadecanoic acid, 19-methylicosanoic acid, and 20-methylhenicosanoic acid, while examples of the anteiso-fatty acid include 16-methyloctadecanoic acid, 17-methylnonadecanoic acid, 18-methylicosanoic acid, and 19-methylhenicosanoic acid. Examples of salts of them include alkali metal salts such as sodium salt and potassium salt, alkaline earth metal salts such as calcium salt and magnesium salt, organic amine salts such as ammonium salt, triethanolamine salt, diethanolamine salt, and monoethanolamine salt, and basic amino acid salts such as lysine salt and arginine salt.

Component (A) is thought to be a compound originally present in the surface of the hair, but it drops off from the hair surface when the hair is subjected to a chemical treatment such as hair dyeing treatment and permanent wave treatment. When the hair grows after such a chemical treatment, two different portions appear, that is, a new growth portion having Component (A) therein and a chemical treated portion having no Component (A) therein. Such hair cannot be dyed uniformly even by the subsequent hair dyeing treatment. Thus, it becomes one of the causes for uneven dyeing. The present invention actualizes uniform hair dyeing by adding Component (A) to the hair surface.

These fatty acids or salts thereof as Component (A) may be used in combination of two or more thereof. The content of this component in the hair dye composition of the present invention is preferably from 0.01 to 10 mass %, more preferably from 0.05 to 5 mass % in order to repair a damaged hair condition and provide excellent hair dyeing properties, particularly, uniform hair dyeing properties.

Component (B) to be used in the present invention is a polymer or copolymer of a diallyl quaternary ammonium salt. The skeleton of the polymer of a diallyl quaternary ammonium salt is preferably represented by the following formula (1) or (2).

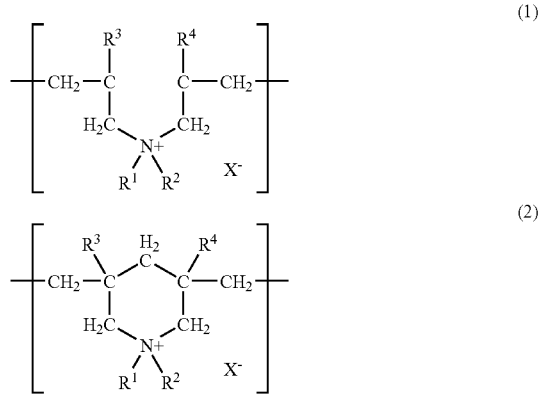

[wherein, $R^1$ and $R^2$ may be the same or different and each represents a hydrogen atom, an alkyl group having from 1 to 18 carbon atoms, an aryl group (such as phenyl group), a hydroxyalkyl group, an amidoalkyl group, a cyanoalkyl group, an alkoxyalkyl group, or a carboalkoxyalkyl group, $R^3$ and $R^4$ may be the same or different and each represents a hydrogen atom, an alkyl group having from 1 to 3 carbon atoms, or a phenyl group, and $X^-$ represents an anion (such as chloride ion, bromide ion, iodide ion, sulfate anion, sulfonate anion, methyl sulfate anion, phosphate anion, or nitrate anion)].

Examples of the monomer constituting a copolymer with the diallyl quaternary ammonium salt include acrylic acid and methacrylic acid, or salts thereof, and acrylamide. Of these, acrylic acid and methacrylic acid, and salts thereof are preferred.

Specific examples of the polymer or copolymer of the diallyl quaternary ammonium salt include dimethyldiallylammonium chloride polymer ("Polyquaternium-6" such as "Merquat 100", product of Nalco), dimethyldiallylammonium chloride/acrylic acid copolymer ("Polyquaternium-22" such as "Merquat 280" and "Merquat 295", each product of Nalco), dimethyldiallylammonium chloride/acrylamide copolymer ("Polyquaternium-7" such as "Merquat 550", product of Nalco), and acrylamide/acrylic acid/dimethyldiallylammonium chloride copolymer (Polyquaternium-39 such as "Merquat Plus 3330" and "Merquat Plus 3331", each product of Nalco). Of these, Polyquaternium-22 (such as "Merquat 280" and "Merquat 295") is preferred.

These polymers or copolymers of the diallyl quaternary ammonium salt as Component (B) may be used in combination of two or more thereof. The content of this component in the hair dye composition of the present invention is preferably from 0.01 to 10 mass %, more preferably from 0.1 to 5 mass %, even more preferably from 0.5 to 3 mass % from the standpoint of improving the feel, enhancing fixation of Component (A) to the hair by forming a complex with Component (A), and retaining a uniformly dyed state for long duration.

[(C) Oxidation Dye]

The hair dye composition of the present invention contains an oxidation dye as Component (C).

As the oxidation dye, known precursors and couplers ordinarily employed for hair dyes are usable. Examples of the precursor include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-paraphenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine, 4,5-diamino-1-(4'-chlorobenzyl)pyrazole, and 4,5-diamino-1-hydroxyethylpyrazole, and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

These precursors and couplers as Component (C) may be used in combination of two or more thereof, respectively, and the content of each of the precursor(s) and the coupler(s) in the hair dye composition of the present invention is preferably from 0.01 to 5 mass %, more preferably from 0.1 to 4 mass %.

As the oxidation dye of Component (C), an air oxidation dye may be usable. Examples of the air oxidation dye include 5,6-dihydroxyindole, 5,6-dihydroxyindole-2-carboxylic acid, 5,6-dihydroxyindoline, and 5,6-dihydroxyindoline-2-carboxylic acid. The air oxidation dye may be used in combination with the precursor and coupler. Alternatively, two or more air oxidation dyes may be used in combination. The content of the air oxidation dye as Component (C) in the hair dye composition of the present invention is preferably from 0.01 to 5 mass %, more preferably from 0.05 to 4 mass %, even more preferably from 0.1 to 3 mass %.

[(D): Alkali Agent]

The hair dye composition of the present invention contains an alkali agent as Component (D). Examples of the alkali agent include ammonia and salts thereof, sodium hydroxide, potassium hydroxide, guanidine, alkanolamines such as monoethanolamine, isopropanolamine, 2-amino-2-methyl-propanol, and 2-aminobutanol and salts thereof, alkanediamines such as 1,3-propanediamine and salts thereof, and carbonates such as guanidine carbonate, sodium carbonate, potassium carbonate, sodium hydrogen carbonate, and potassium hydrogen carbonate.

These alkali agents as Component (D) may be used in combination of two or more thereof. The content of this component in the hair dye composition of the present invention is preferably from 0.05 to 15 mass %, more preferably from 0.1 to 10 mass %, even more preferably from 0.2 to 5 mass % from the standpoint of a sufficient hair-dyeing effect and reduction of hair damage and scalp stimulation.

[(E): Silicone]

The hair dye composition of the present invention preferably contains a silicone further as Component (E). Examples of the silicone include the following silicone (E-i) to (E-vi).

(E-i) Highly Polymerized Dimethylpolysiloxane Represented by the Following Formula:

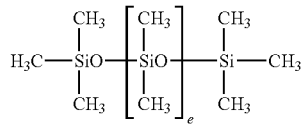

[wherein, e stands for an integer from 650 to 20000].

Examples of commercially available products of it include "BY11-026" and "BY22-19" (each, product of Dow Corning Toray) and "FZ-3125" (product of Nippon Unicar).

The highly polymerized dimethylpolysiloxane dissolved or dispersed in a liquid oil (for example, liquid silicone oil described below such as (E-ii) dimethylpolysiloxane oil or (E-iii) cyclic silicone oil, or liquid hydrocarbon oil such as isoparaffin) can also be used.

(E-ii) Dimethylpolysiloxane Oil Represented by the Following Formula:

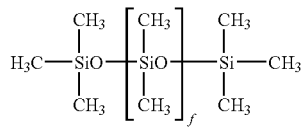

[wherein, f stands for an integer from 0 to 649].

Examples of the commercially available product thereof include "SH200C Series" having a viscosity of 1 cs, 50 cs, 200 cs, 1000 cs and 5000 cs, respectively (Dow Corning Toray).

(E-iii) Cyclic Silicone Represented by the Following Formula:

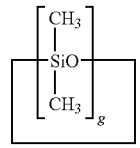

[wherein, g stands for an integer from 3 to 7].

Specific examples include dodecamethylcyclohexasiloxane, octamethylcyclotetrasiloxane, and decamethylcyclopentasiloxane. Examples of the commercially available product include "SH244" and "SH245" (each, product of Dow Corning Toray).

(E-iv) Amino-Modified Silicone Represented by the Following Formula:

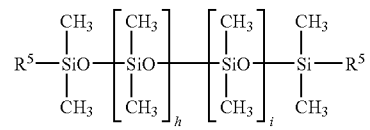

[wherein, $R^5$ and $R^6$ represent the same group, a methyl group, or a hydroxyl group, $R^6$ represents a reactive functional group represented by —$R^7$-Q (in which $R^7$ represents a divalent hydrocarbon group having from 3 to 6 carbon atoms, and Q represents a group containing a primary, secondary or tertiary amino group or an ammonium-containing group), and h and i each stands for a positive integer and h+i varies depending on the molecular weight. The average molecular weight is preferably from 3000 to 100000].

Examples of commercially available products include "SS-3551", "SF8452C", "DC929", and "DC8500" (each, product of Down Corning Toray) and "KT 1989" (product of Momentive Performance Materials). When the amino-modified silicone is used in the form of an aqueous emulsion, the amount of the amino-modified silicone contained in the aqueous emulsion is preferably from 20 to 60 mass %, more preferably from 30 to 50 mass %. Preferred examples of the aqueous emulsion of an amino-modified silicone include "SM8704C" (product of Dow Corning Toray).

(E-v) Polyether-Modified Silicone

It is dimethylpolysiloxane having a main chain to which a polyoxyalkylene group, preferably a polyoxyethylene group or polyoxypropylene group has been attached.

Examples of the commercially available product of include "Silicone KF6011", "Silicone KF6012", "Silicone KF6013", "Silicone KF351A", "Silicone KF352A", and "Silicone KF615A" (each, product of Shin-etsu Chemical), and "Silicone SH3746", "Silicone SH3771C", and "Silicone SH3749" (each, product of Dow Corning Toray).

(E-vi) Other Silicone

Additional examples include methylphenylpolysiloxane, fatty acid-modified silicone, alcohol-modified silicone, alkoxy-modified silicone, epoxy-modified silicone, fluorine-modified silicone, and alkyl-modified silicone.

These silicone as Component (E) may be used in combination of two or more thereof. The content of this component in the hair dye composition of the present invention is preferably from 0.1 to 15 mass %, more preferably from 0.5 to 10 mass %, even more preferably from 1 to 7 mass % from the standpoint of providing the hair with good feel.

[(F): Cationic Surfactant]

The hair dye composition of the present invention preferably contains a cationic surfactant further as Component (F). The term "cationic surfactant" as used herein means a concept embracing a quaternary ammonium salt and a tertiary amine and salt thereof. Examples of the cationic surfactant include quaternary ammonium salts represented by the following formula:

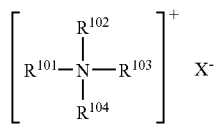

[wherein, at least one of $R^{101}$, $R^{102}$, $R^{103}$, and $R^{104}$ represents an alkyl or alkenyl group which may be substituted with an alkoxy group, an alkenyloxy group, an alkanoylamino group, or an alkenoylamino group so as to adjust the total number of carbon atoms including the number of carbon atoms of the substituent to fall within a range from 8 to 40 and remaining one(s) represent(s) a benzyl group, an alkyl or hydroxyalkyl group having from 1 to 5 carbon atoms, or a polyoxyalkylene group having an average number of moles added of from 1 to 6, and $X^-$ represents a halide ion (chloride ion, bromide ion, or the like) or an organic anion (methyl sulfate ion, ethyl sulfate ion, methyl carbonate ion, saccharin ion, or the like)].

Additional examples include tertiary amines represented by the following formula and salts thereof.

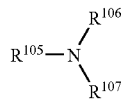

[wherein, at least one of $R^{105}$, $R^{106}$, and $R^{107}$ represents an alkyl or alkenyl group which may be substituted with an alkoxy group, an alkenyloxy group, an alkanoylamino group, or an alkenoylamino group so as to adjust the total number of carbon atoms including the number of carbon atoms of the substituent to fall within a range from 8 to 40 and remaining one(s) represent(s) an alkyl or hydroxyalkyl group having from 1 to 6 carbon atoms or a polyoxyalkylene group having an average number of moles added of from 1 to 6].

Of these, for example, the following compounds (F-i) to (F-iv) are preferred.

(F-i) Alkyltrimethylammonium Salt Type

Examples of it include compounds represented by the following formula:

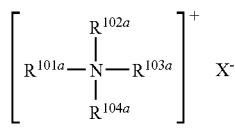

[wherein, $R^{101a}$ represents a linear or branched alkyl or alkenyl group having from 8 to 40 carbon atoms, $R^{102a}$, $R^{103a}$, and $R^{104a}$ may be the same or different and each represents an alkyl or hydroxyalkyl group having from 1 to 6 carbon atoms, a benzyl group, or —$(A^1O)_aH$ (in which $A^1$ represents an alkylene group having from 2 to 4 carbon atoms, an average number of moles added "a" represents the number from 1 to 6, and "a" pieces of $A^1O$ may be the same or different and may be arranged in any order), and $X^-$ has the same meaning as described above].

In the above formula, $R^{101a}$ is preferably a linear or branched alkyl group having from 12 to 28, more preferably from 16 to 22 carbon atoms. $R^{102a}$ and $R^{104a}$ are each preferably an alkyl group having from 1 to 3 carbon atoms, a hydroxyalkyl group having from 2 to 3 carbon atoms, or —$(CH_2CH_2O)_aH$ (an average number of moles added "a" is preferably from 1 to 3, more preferably from 1 to 2). Of these, methyl and ethyl groups are more preferred, with a methyl group being even more preferred. $R^{103a}$ is preferably a methyl group, an ethyl group, or a benzyl group, more preferably a methyl group or an ethyl group, even more preferably a methyl group. $X^-$ is preferably a chlorine ion or a bromine ion.

Specific examples include lauryltrimethylammonium chloride, myristyltrimethylammonium chloride, cetyltrimethylammonium chloride, cetyltrimethylammonium bromide, stearyltrimethylammonium chloride, stearyltrimethylammonium bromide, arachyltrimethylammonium chloride, bephenyltrimethylammonium chloride, isostearyltrimethylammonium chloride, 2-octyldodecyltrimethylammonium chloride, and 2-decyltetradecyltrimethylammonium chloride.

(F-ii) Alkoxytrimethylammonium Salt Type

Examples of it include compounds represented by the following formula:

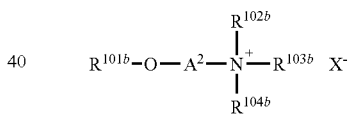

[wherein, $R^{101b}$ represents a linear or branched alkyl or alkenyl group having from 6 to 28 carbon atoms, $R^{102b}$, $R^{103b}$, and $R^{104b}$ may be the same or different and each represents an alkyl or hydroxyalkyl group having from 1 to 6 carbon atoms, a benzyl group, or —$(A^3O)_bH$ (in which $A^3$ represents an alkylene group having from 2 to 4 carbon atoms, an average number of moles added "b" represents the number from 1 to 6, and "b" pieces of $A^3O$ may be the same or different and may be arranged in any order), $A^2$ represents a linear or branched alkylene group having from 2 to 5 carbon atoms, and $X^-$ has the same meaning as described above].

In the above formula, $R^{101b}$ is preferably a linear or branched alkyl or alkenyl group having from 12 to 22, more preferably from 16 to 18 carbon atoms, of which the linear alkyl group is preferred. $R^{102b}$ and $R^{104b}$ are each preferably an alkyl group having from 1 to 3 carbon atoms, a hydroxyalkyl group having from 2 to 3 carbon atoms, or —$(CH_2CH_2O)_bH$ (an average number of moles added "b" is preferably from 1 to 3, more preferably from 1 to 2). Of these, methyl and ethyl groups are more preferred, with a methyl group being even more preferred. $R^{103b}$ is preferably a methyl group, an ethyl group, or a benzyl group, more preferably a methyl group and an ethyl group, even more preferably a methyl group. $A^2$ is preferably an ethylene group or an n-propylene group. $X^-$ is preferably a chlorine ion, a bromine ion, or an ethyl sulfate ion.

Specific examples include 3-hexadecyloxypropyl-N,N,N-trimethylammonium chloride, 3-octadecyloxypropyl-N,N,N-trimethylammonium chloride, 3-hexadecyloxyethyl-N,N,N-trimethylammonium chloride, and 3-octadecyloxyethyl-N,N,N-trimethylammonium chloride.

(F-iii) Alkylamidotrimethylammonium Salt Type

Examples of it include compounds represented by the following formula:

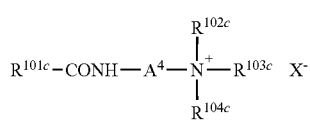

[wherein, $R^{101c}$ represents a linear or branched alkyl or alkenyl group having from 7 to 37 carbon atoms, $R^{102c}$, $R^{103c}$, and $R^{104c}$ may be the same or different and each represents an alkyl or hydroxyalkyl group having from 1 to 6 carbon atoms, a benzyl group, or $-(A^5O)_cH$ (in which $A^5$ represents an alkylene group having from 2 to 4 carbon atoms, an average number of moles added "c" stands for 1 to 6, and "c" pieces of $A^5O$ may be the same or different and may be arranged in any order), $A^4$ represents a linear or branched alkylene group having from 2 to 5 carbon atoms, and $X^-$ has the same meaning as described above].

In the above formula, $R^{101c}$ is preferably a linear or branched alkyl group having from 8 to 21, more preferably from 11 to 18 carbon atoms. $R^{102c}$ and $R^{104c}$ are each preferably an alkyl group having from 1 to 3 carbon atoms, a hydroxyalkyl group having from 2 to 3 carbon atoms, or $-(CH_2CH_2O)_cH$ (an average number of moles added "c" is preferably from 1 to 3, more preferably from 1 to 2). Of these, methyl and ethyl groups are more preferred, with a methyl group being more preferred. $R^{103c}$ is preferably a methyl group, an ethyl group, or a benzyl group, more preferably a methyl group or an ethyl group, even more preferably a methyl group. $A^4$ is preferably an ethylene group or an n-propyl group. $X^-$ is preferably a chlorine ion, a bromine ion, a methyl sulfate ion, an ethyl sulfate ion, or a methyl carbonate ion. An alkanoyl group $R^{101c}$—CO— is preferably derived from lanolin.

Specific examples include lanolin fatty acid aminopropylethyldimethylammonium ethyl sulfate (ethyl sulfate of alkanoyl aminopropyldimethylethylammonium, the alkanoyl group of which is derived from lanolin), lanolin fatty acid aminoethyltriethylammonium ethyl sulfate, lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic acid (from $C_{14}$ to $C_{20}$) aminopropylethyldimethylammonium ethyl sulfate, isoalkanoic acid (from $C_{18}$ to $C_{22}$) aminopropylethyldimethylammonium ethyl sulfate, isostearic acid aminopropylethyldimethylammonium ethyl sulfate, and isononanoic acid aminopropylethyldimethylammonium ethyl sulfate.

(F-iv) Dialkyldimethylammonium Salt Type

Examples of it include compounds represented by the following formula:

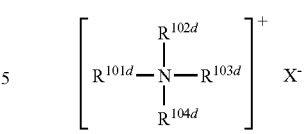

[wherein, $R^{101d}$ and $R^{102d}$ may be the same or different and each represents a linear or branched alkyl or alkenyl group having from 8 to 40 carbon atoms, $R^{103d}$ and $R^{104d}$ may be the same or different and each represents an alkyl or hydroxyalkyl group having from 1 to 6 carbon atoms, a benzyl group, or $-(A^6O)_dH$ (in which $A^6$ represents an alkylene group having from 2 to 4 carbon atoms, "d" represents an average number of moles added from 1 to 6, and "d" pieces of $(A^6O)$s may be the same or different and may be arranged in any order), and $X^-$ has the same meaning as described above].

In the above formula, $R^{101d}$ and $R^{102d}$ are each preferably a linear or branched alkyl group having from 12 to 28, more preferably from 16 to 22 carbon atoms. $R^{103d}$ and $R^{104d}$ are each preferably an alkyl group having from 1 to 3 carbon atoms, a hydroxyalkyl group having from 2 to 3 carbon atoms, or $-(CH_2CH_2O)_dH$ (an average number of moles added "d" is preferably from 1 to 3, more preferably from 1 to 2). Of these, methyl and ethyl groups are more preferred, with a methyl group being even more preferred. $X^-$ is preferably a chlorine ion or a bromine ion.

Specific examples include dialkyl (from 12 to 18) dimethylammonium chlorides, dicetyldimethylammonium chloride, distearyldimethylammonium chloride, di-2-hexyldecyldimethylammonium chloride, and di-2-octyldodecyldimethylammonium chloride.

(F-v) Alkyldimethylamine Type

Examples include compounds represented by the following formula and organic acid salts or inorganic acid salts thereof.

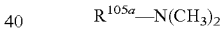

[wherein, $R^{105a}$ represents a linear or branched alkyl or alkenyl group having from 12 to 28 carbon atoms].

Specific examples include N,N-dimethylhexadecylamine and N,N-dimethyloctadecylamine.

(F-vi) Alkylamidoamine Type

Examples include compounds represented by the following formula and organic acid salts or inorganic acid salts thereof.

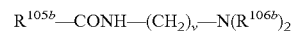

[wherein, $R^{105b}$ represents a linear or branched alkyl or alkenyl group having from 11 to 37 carbon atoms, $R^{106b}$ may be the same or different and each represents a hydrogen atom or an alkyl group having from 1 to 4 carbon atoms, and v stands for the number from 2 to 4].

Specific examples include dimethylaminoethylamide stearate, dimethylaminopropylamide stearate, diethylaminoethylamide stearate, diethylaminopropylamide stearate, dipropylaminoethylamide stearate, dipropylaminopropylamide stearate, dimethylaminoethylamide palmitate, dimethylaminopropylamide palmitate, dimethylaminoethylamide myristate, dimethylaminorpopylamide myristate, dimethylaminoethylamide behenate, dimethylaminopropylamide behenate, dimethylaminoethylamide arachidate, and dimethylaminopropylamide arachidate.

(F-vii) Alkyletheramine Type

Examples include compounds represented by the following formula and organic acid salts or inorganic acid salts thereof.

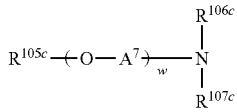

[wherein, $R^{105c}$ represents a linear or branched alkyl or alkenyl group having from 6 to 28 carbon atoms, $A^7$ represents a linear or branched alkylene group having from 2 to 5 carbon atoms, $R^{106c}$ and $R^{107c}$ may be the same or different and each represents an alkyl group having from 1 to 6 carbon atoms or —$(A^8O)_xH$ (in which $A^8$ represents an alkylene group having from 2 to 4 carbon atoms, (x) stands for the number from 1 to 6, and (x) pieces of $A^8$ may be the same or different and may be arranged in any order), and w stands for an integer from 1 to 8].

Specific examples include N,N-dimethyl-3-hexadecyloxypropylamine, N,N-dimethyl-3-octadecyloxypropylamine, N,N-dimethyl-stearyldiethoxyamine, N,N-dimethyl-stearyltriethoxyamine, N,N-dimethyl-behenyldiisopropyloxyamine, and N,N-dimethyl-behenyltriisopropyloxyamine.

(F-viii) Hydroxyetheralkylamine Type

Examples include compounds represented by the following formula and organic acid salts or inorganic acid salts thereof.

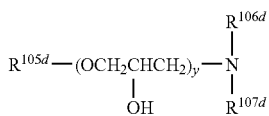

[wherein, $R^{105d}$ represents a linear or branched alkyl or alkenyl group having from 8 to 24 carbon atoms, $R^{106d}$ and $R^{107d}$ may be the same or different and each represents an alkyl group having from 1 to 6 carbon atoms or —$(A^9O)_zH$ (in which $A^9$ represents an alkylene group having from 2 to 4 carbon atoms, (z) stands for the number from 1 to 6, and (z) pieces of $A^9$ may be the same or different and may be arranged in any order), and y stands for the number from 1 to 5].

Specific examples include hexadecyloxy(2-hydroxypropyl)dimethylamine, octadecyloxy(2-hydroxypropyl)dimethylamine, and bephenyloxy(2-hydroxypropyl)dimethylamine.

Of these, the quaternary ammonium salts are preferred because the complex formed with Component (A) improves fixation to the hair and improves durability of its effect.

These cationic surfactants as Component (F) may be used in combination of two or more thereof. The content of this component in the hair dye composition of the present invention is preferably from 0.01 to 10 mass %, more preferably from 0.05 to 5 mass % from the standpoint of contributing to emulsion stability of the composition and improving the feel.

A ratio (A)/(F), that is, a Component (A)/Component (F) mass ratio in the hair dye composition of the present invention is adjusted to fall within a range of preferably from 50/1 to 1/50, more preferably from 10/1 to 1/10, even more preferably from 5/1 to 1/5, even more preferably from 2/1 to 1/2, because within the above-described range, Component (A) and Component (F) form a complex, thereby accelerating more firm fixing of Component (A) to the hair and improving durability of the uniformly dyed state.

[(G): Polyoxyethylene Alkyl Ether Type Nonionic Surfactant]

The hair dye composition of the present invention preferably contains a polyoxyethylene alkyl ether type nonionic surfactant further as Component (G). The alkyl group of the surfactant is preferably linear and has preferably from 12 to 30 carbon atoms, more preferably from 16 to 22 carbon atoms. The number average polymerization degree of the oxyethylene group of it is preferably from 1 to 50, more preferably from 2 to 40.

Specific examples include polyoxyethylene (4) lauryl ether, polyoxyethylene (9) lauryl ether, polyoxyethylene (23) lauryl ether, polyoxyethylene (2) cetyl ether, polyoxyethylene (5) cetyl ether, polyoxyethylene (10) cetyl ether, polyoxyethylene (20) cetyl ether, polyoxyethylene (30) cetyl ether, polyoxyethylene (40) cetyl ether, polyoxyethylene (5) stearyl ether, polyoxyethylene (20) stearyl ether, polyoxyethylene (5) behenyl ether, polyoxyethylene (30) behenyl ether, polyoxyethylene (20) 2-octyldodecyl ether, polyoxyethylene (3) tridecyl ether, and polyoxyethylene (9) tridecyl ether.

These polyoxyethylene alkyl ether type nonionic surfactants as Component (G) may be used in combination of two or more thereof. The content of this component in the hair dye composition of the present invention is preferably from 0.1 to 20 mass %, more preferably from 0.5 to 15 mass % from the standpoint of improving the stability of the composition. In addition, it is preferred to incorporate Component (G) and Component (A) in the same agent from the standpoint of storage stability.

An (A)/(G) mass ratio, that is, a Component (A)/Component (G) mass ratio is adjusted to fall within a range of preferably from 50/1 to 1/50, more preferably from 10/1 to 1/10 from the standpoint of stabilizing the complex of Component (A) and Component (B) in the composition, thereby improving a repairing effect of damaged hair and improving a dyeing effect for uniform dyeing or the like.

A (F)/(G) mass ratio, that is, a Component (F)/Component (G) mass ratio is adjusted to fall within a range of preferably from 50/1 to 1/50, more preferably from 10/1 to 1/10.

[(H): Hydrocarbon in Liquid, Semi-Solid, or Solid Form]

The hair dye composition of the present invention preferably contains a hydrocarbon in liquid, semi-solid, or solid form at 25° C. further as Component (H). Examples of such a hydrocarbon include α-olefin oligomer, light isoparaffin, light liquid isoparaffin, squalane, squalene, polybutene, liquid isoparaffin, and liquid paraffin which are in liquid form at 25° C.; and ozokerite, ceresin, paraffin, powdered polyethylene, microcrystalline wax, and vaseline which are in solid form at 25° C.

These hydrocarbons in liquid, semi-solid or solid form at 25° C. as Component (H) may be used in combination of two or more thereof. The content of this component in the hair dye composition of the present invention is preferably from 0.1 to 30 mass %, more preferably from 0.5 to 20 mass %, even more preferably from 1 to 10 mass % from the standpoint of enhancing emulsion stability of the composition and preventing emission of an irritating odor.

[(I): Fatty Alcohol]

The hair dye composition of the present invention preferably contains a fatty alcohol further as Component (I). The fatty alcohol has preferably from 12 to 30 carbon atoms, more preferably from 16 to 22 carbon atoms.

Specific examples of it include lauryl alcohol, myristyl alcohol, cetyl alcohol, stearyl alcohol, arachyl alcohol, behenyl alcohol, isostearyl alcohol, 2-octyldodecanol, and oleyl alcohol.

These fatty alcohols as Component (I) may be used in combination of two or more thereof. The content of it in the hair dye composition of the present invention is preferably from 0.1 to 20 mass %, more preferably from 0.5 to 15 mass %, even more preferably from 1 to 10 mass %, because the resulting composition has excellent emulsion stability.

[(J): Coenzyme Q]

The hair dye composition of the present invention preferably contains a coenzyme Q further as Component (J). The coenzyme Q has an oxidation type coenzyme Q represented by the formula (J-1) and a reduction type coenzyme Q represented by the formula (J-2). Of these, the coenzymes Q with j being 10, that is, oxidation type coenzyme $Q_{10}$ and reduction type coenzyme $Q_{10}$ are preferred.

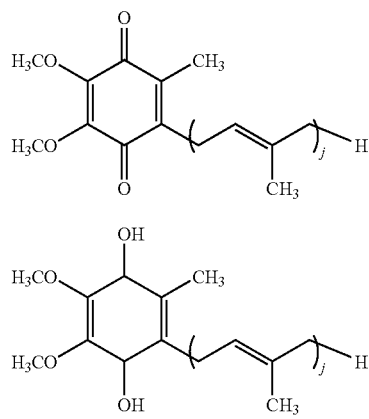

(J-1)

(J-2)

[wherein, j stands for an integer from 1 to 12].

The coenzymes Q as Component (J) may be used in combination of two or more thereof. Only the oxidation type or only the reduction type may be used, but alternatively both may be used in combination. The content of this component in the hair dye composition of the present invention is preferably from 0.00001 to 1 mass %, more preferably from 0.0001 to 0.8 mass %, even more preferably from 0.001 to 0.5 mass % from the standpoint of improving the shampoo fastness and stability of the composition.

[(K): Betaine Compound or Acid Addition Salt Thereof]

The hair dye composition of the present invention preferably contains further as Component (K) a betaine compound represented by the following formula or acid addition salt thereof.

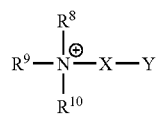

[wherein, $R^8$, $R^9$ and $R^{10}$ may be the same or different and each represents an alkyl group having from 1 to 3 carbon atoms, X represents an alkylene group having from 1 to 3 carbon atoms, and Y represents $CO_2^-$, $SO_3^-$, $OSO_3^-$, or $OPO_3^-$].

These betaine compounds are compounds in which an amphoteric ion is formed by an intramolecular salt between a quaternary ammonium cation group and a carboxy anion group, sulfo anion group, sulfate anion group, or phosphate anion group. The term "acid-addition salt of the betaine compound" as used herein means an addition salt of a physiologically acceptable organic acid or inorganic acid. The inorganic acid is preferably hydrochloric acid, sulfuric acid, or phosphoric acid, while the organic acid is preferably tartaric acid, malic acid, benzoic acid, or salicylic acid. It is more preferably hydrochloric acid, sulfuric acid, or phosphoric acid.

Specific examples include betaine compounds having a structure shown below and addition salts thereof. Of these, glycine betaine is preferred.

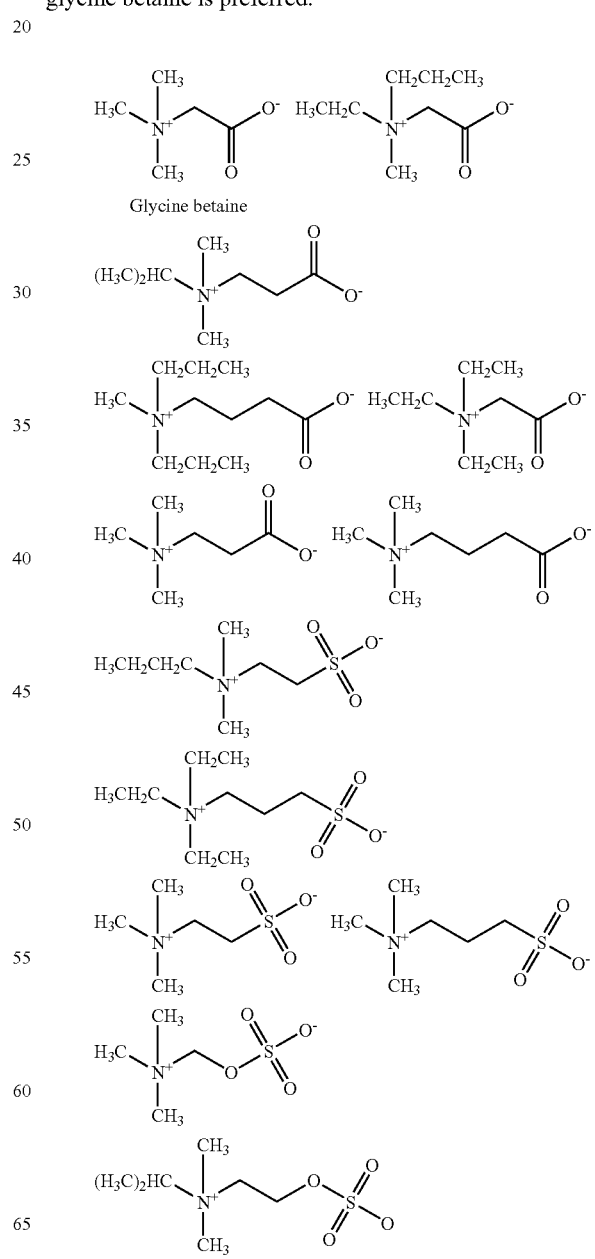

Glycine betaine

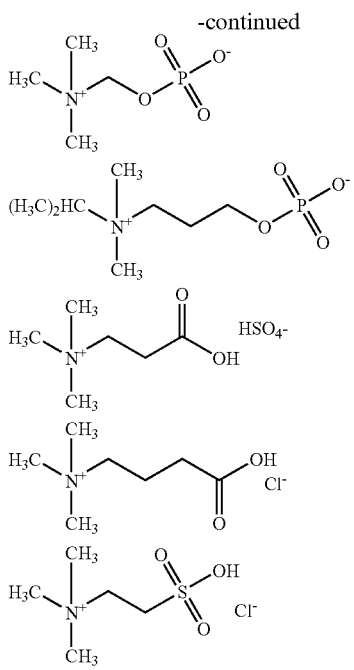

These betaine compounds or acid addition salts thereof as Component (K) may be used in combination of two or more thereof. The content of this component in the hair dye composition of the present invention is preferably from 0.01 to 20 mass %, more preferably from 0.05 to 10 mass %, even more preferably from 0.1 to 5 mass % from the viewpoint of excellent effects for preventing hair damage, improving manageability of the hair, and dyeing the hair uniformly.

[(L): Amphipathic Amide Lipid]

The hair dye composition of the present invention preferably contains an amphipathic amide lipid further as Component (L). Examples of the amphipathic amide lipid include those selected from diamide compounds represented by the formula (L-1) and ceramides represented by the formula (L-2).

(L-i) Diamide Compound Represented by the Formula (L-1)

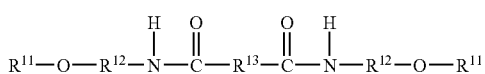

(L-1)

[wherein, $R^{11}$ represents a linear or branched hydrocarbon group which has from 1 to 12 carbon atoms and may be substituted with a hydroxy group and/or alkoxy group, $R^{12}$ represents a linear or branched divalent hydrocarbon group having from 1 to 5 carbon atoms, and $R^{13}$ represents a linear or branched divalent hydrocarbon group having from 1 to 22 carbon atoms].

In the formula (L-1), $R^{11}$ represents preferably a linear or branched alkyl group which has from 1 to 12 carbon atoms and may be substituted with 1 to 3 groups selected from a hydroxy group and alkoxy groups having from 1 to 6 carbon atoms. Of these, unsubstituted alkyl groups having from 1 to 12 carbon atoms and alkyl groups which have from 2 to 12 carbon atoms and have been substituted with one or two hydroxy groups or one alkoxy group having from 1 to 6 carbon atoms or with one hydroxy group and one alkoxy group having from 1 to 6 carbon atoms are more preferred. Specific examples include methyl, ethyl, propyl, butyl, hexyl, dodecyl, 2-methylpropyl, 2-ethylhexyl, 2-hydroxyethyl, 9-hydroxynonyl, 2,3-dihydroxypropyl, 2-methoxyethyl, 2-hydroxy-3-methoxypropyl, and 9-methoxynonyl groups, of which 2-hydroxyethyl, methyl, dodecyl, and 2-methoxyethyl groups are preferred.

In the formula (L-1), $R^{12}$ represents a linear or branched alkylene group having preferably from 2 to 5 carbon atoms, more preferably from 2 to 3 carbon atoms. Specific examples include ethylene, trimethylene, tetramethylene, pentamethylene, 1-methylethylene, 2-methylethylene, 1-methyltrimethylene, 2-methyltrimethylene, 1,1-dimethylethylene, and 2-ethyltrimethylene groups. Of these, ethylene and trimethylene groups are preferred.

In the formula (L-1), $R^{13}$ represents preferably a linear or branched divalent hydrocarbon group having from 2 to 22 carbon atoms, more preferably a linear or branched alkylene group having from 11 to 22 carbon atoms or an alkenylene group having from 1 to 4 double bonds. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, ethenylene, 1-octadecenylethylene, 7,11-octadecadienylene, 7-ethenyl-9-hexadecamethylene, 7,12-dimethyl-7,11-octadecadienylene, and 8,11-dimethyl-7,11-octadecadienylene groups. Of these, 7,12-dimethyloctadecamethylene, 7,12-dimethyl-7,11-octadecadienylene, octadecamethylene, undecamethylene, and tridecamethylene groups are preferred.

More preferred diamide compounds (L-1) are compounds having the above-described preferred groups as $R^{11}$, $R^{12}$ and $R^{13}$, respectively, in combination. Specific examples are the following compounds:

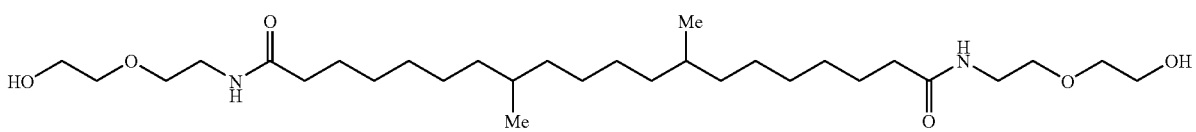

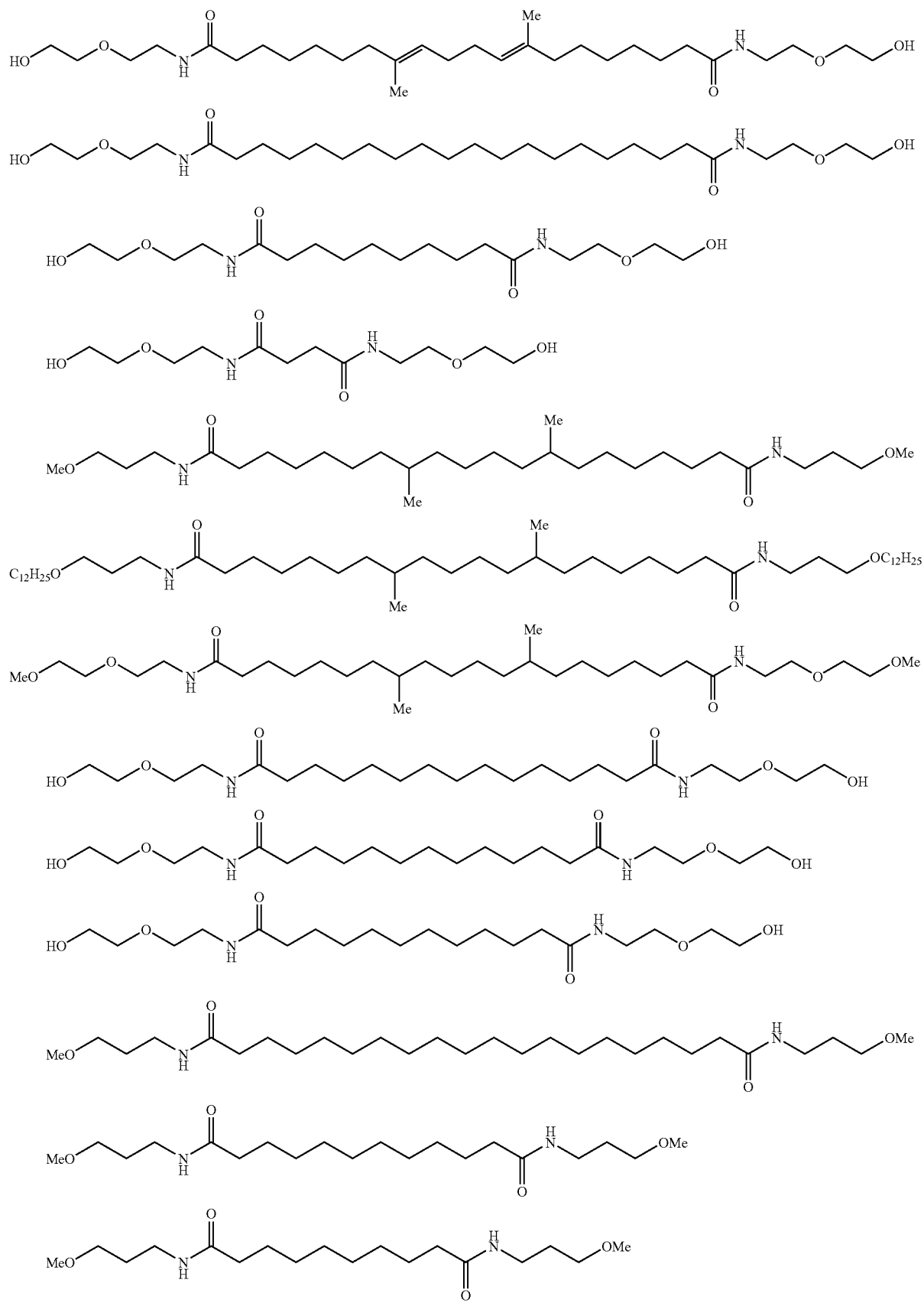

-continued

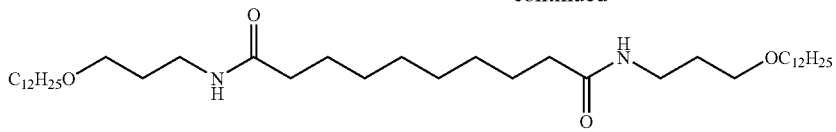

(L-ii) Ceramides Represented by the Formula (L-2):

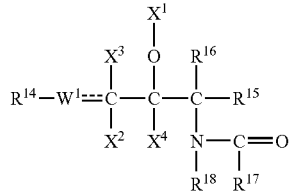
(L-2)

[wherein, $R^{14}$ represents a linear, branched or cyclic, saturated or unsaturated hydrocarbon group which has from 4 to 30 carbon atoms and may be substituted with a hydroxy, oxo, or amino group; W represents a methylene group, a methine group, or an oxygen atom; a broken line represents the presence or absence of a n bond; $X^1$ represents a hydrogen atom, an acetyl group, or a glyceryl group, or forms an oxo group together with the adjacent oxygen atom; $X^2$, $X^3$ and $X^4$ each independently represent a hydrogen atom, a hydroxy group, or an acetoxy group (with the proviso that when W represents a methine group, either one of $X^2$ or $X^3$ represents a hydrogen atom and the other does not exist, and when —O—$X^1$ represents an oxo group, $X^4$ does not exist); $R^{15}$ and $R^{16}$ each independently represents a hydrogen atom, a hydroxy group, a hydroxymethyl group, or an acetoxymethyl group; $R^{17}$ represents a linear, branched or cyclic, saturated hydrocarbon group which has from 5 to 35 carbon atoms and may be substituted with a hydroxy or amino group, or the hydrocarbon group having, ester-bonded to the ω-position thereof, a linear, branched, or cyclic, saturated or unsaturated fatty acid which has from 8 to 22 carbon atoms and may be substituted with a hydroxy group; and $R^{18}$ represents a hydrogen atom or a linear or branched, saturated or unsaturated hydrocarbon group which may have a substituent selected from a hydroxy group, hydroxyalkoxy groups, alkoxy groups, and an acetoxy group and has from 1 to 8 carbon atoms in total).

In the formula (L-2), $R^{14}$ is preferably a linear, branched or cyclic, saturated or unsaturated hydrocarbon groups which has from 7 to 22 carbon atoms and may be substituted with a hydroxy group. $X^1$ is preferably a hydrogen atom or a glyceryl group. It is preferred that at most one of $X^2$, $X^3$, and $X^4$ represents a hydroxy group and the others represent a hydrogen atom. As $R^{15}$ and $R^{16}$, preferably one of them represents a hydrogen atom or a hydroxymethyl group and the other represents a hydrogen atom. In $R^{17}$, the fatty acid which may be ester-bonded or amide-bonded to the ω-position of the saturated hydrocarbon group is preferably isostearic acid, 12-hydroxystearic acid or linoleic acid. $R^{18}$ is preferably a hydrogen atom or a hydrocarbon group which may be substituted with 1 to 3 substituents selected from a hydroxy group, hydroxyalkoxy groups, and alkoxy groups and has from 1 to 8 carbon atoms in total.

As the ceramide (L-2), preferred are natural ceramides and natural type ceramides, and derivatives thereof (which will hereinafter be called "natural type ceramides (L-2a)") each represented by the following formula (L-2a) and pseudo type ceramides represented by the formula (L-2b) (which will hereinafter be called "pseudo type ceramides (L-2b)").

(L-iia) Natural Type Ceramides (L-2a)

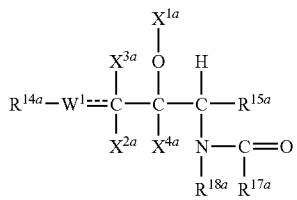
(L-2a)

[wherein, $R^{14a}$ represents a linear, branched or cyclic, saturated or unsaturated hydrocarbon group which has from 7 to 19 carbon atoms and may be substituted with a hydroxy group; $W^1$ represents a methylene or methine group; a broken line represents the presence or absence of a π bond; $X^{1a}$ represents a hydrogen atom or forms an oxo group together with the adjacent oxygen atom; $X^{2a}$, $X^{3a}$ and $X^{4a}$ each independently represents a hydrogen atom, a hydroxy group, or an acetoxy group (with the proviso that when $W^1$ represents a methine group, one of $X^{2a}$ and $X^{3a}$ represents a hydrogen atom and the other does not exist, and when —O—$X^{1a}$ represents an oxo group, $X^{4a}$ does not exist); $R^{15a}$ represents a hydroxymethyl group or an acetoxymethyl group; $R^{17a}$ represents a linear, branched, or cyclic, saturated hydrocarbon group which has from 5 to 30 carbon atoms and may be substituted with a hydroxy group or the hydrocarbon group having, ester-bonded to the ω-position of the alkyl group thereof, a linear or branched, saturated or unsaturated fatty acid which has from 8 to 22 carbon atoms and may be substituted with a hydroxy group; and $R^{18a}$ represents a hydrogen atom or an alkyl group having from 1 to 4 carbon atoms].

Preferred are compounds in which $R^{14a}$ is a linear alkyl group having from 7 to 19 carbon atoms, more preferably from 13 to 15 carbon atoms; $W^1$ is a methine group and either one of $X^{2a}$ and $X^{3a}$ is a hydrogen atom; and $R^{17a}$ is a linear alkyl group which has from 9 to 27 carbon atoms and may be substituted with a hydroxy group. In addition, $X^{1a}$ preferably represents a hydrogen atom, or forms an oxo group together with an oxygen atom. $R^{17a}$ preferably represents a tricosyl group, a 1-hydroxypentadecyl group, a 1-hydroxytricosyl group, a heptadecyl group, a 1-hydroxyundecyl group, or a nonacosyl group having linoleic acid ester-bonded to the ω-position thereof.

Specific examples of the natural type ceramides include Ceramide Types 1 to 7 having the structures as described below obtained by amidation of sphingosine, dihydrosphingosine, phytosphingosine or sphingadienine (for example, FIG. 2 of J. Lipid Res., 24: 759 (1983), and pig and human ceramides as described in FIG. 4 of J. Lipid Res., 35: 2069 (1994)) and N-alkyl derivatives (for example, N-methyl derivatives) thereof. They may be either a natural extract or synthesized product. Commercially available ones can also be used.

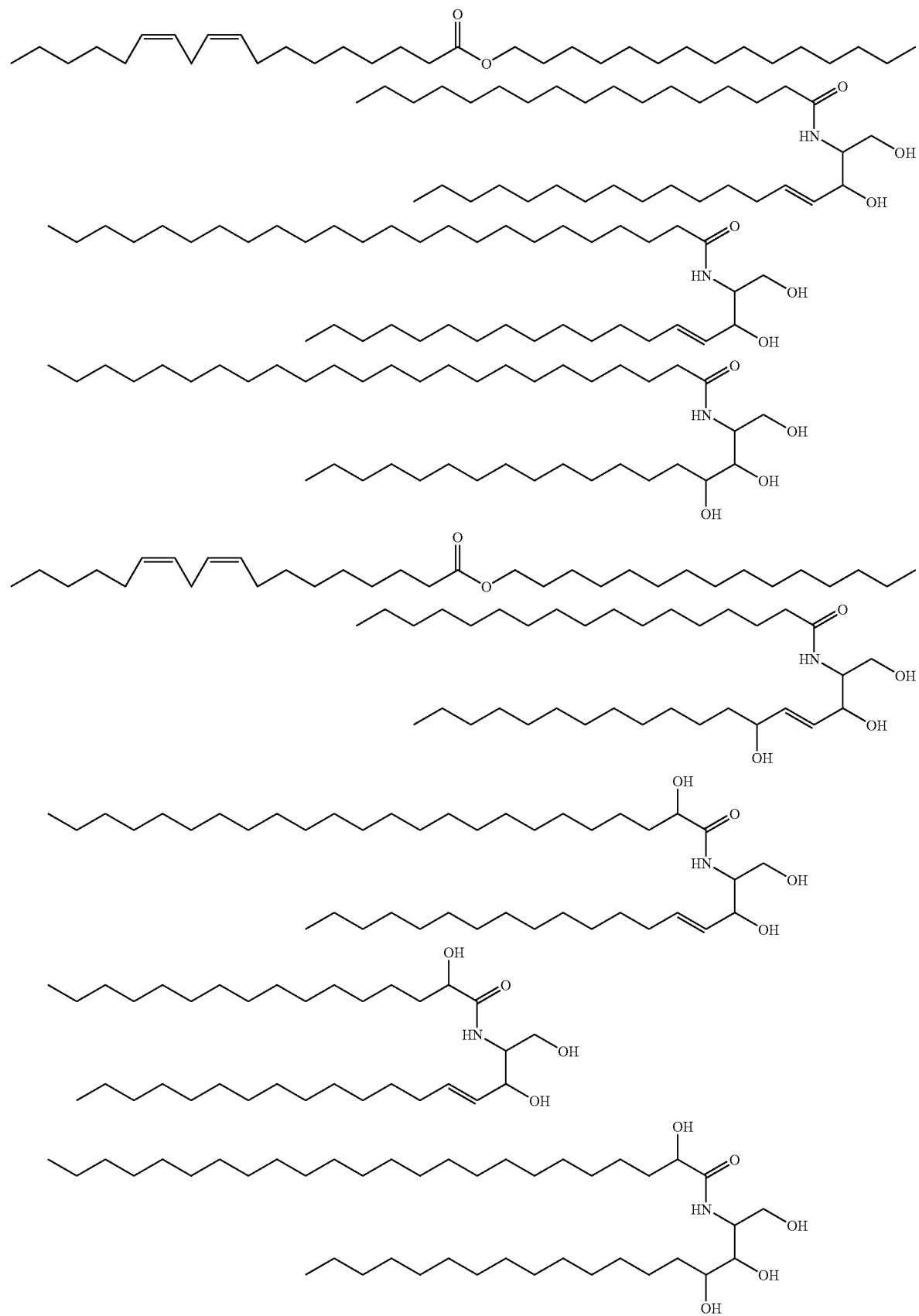

-continued

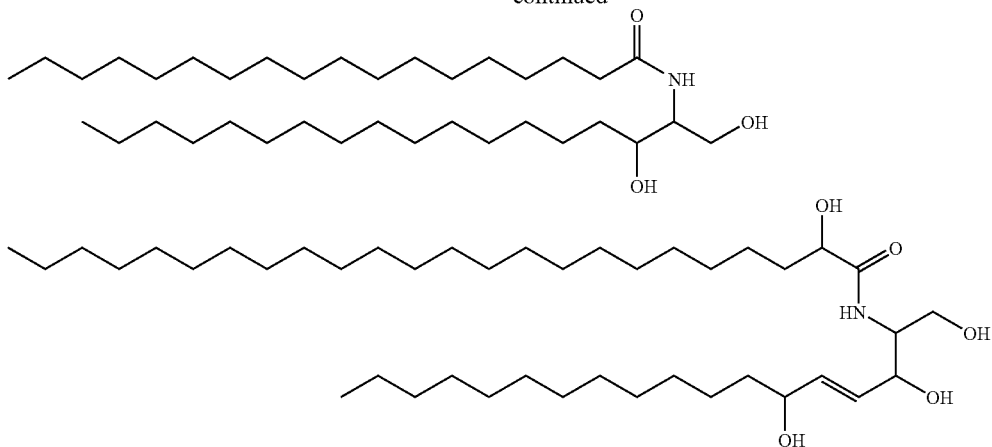

(L-iib) Pseudo Type Ceramides (L-2b)

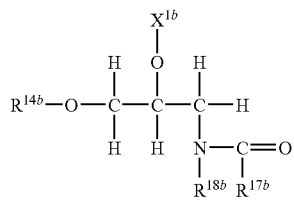

(L-2b)

[wherein, $R^{14b}$ represents a linear, branched or cyclic, saturated or unsaturated hydrocarbon group which has from 10 to 22 carbon atoms and may be substituted with a hydroxy group; $X^{1b}$ represents a hydrogen atom, an acetyl group, or a glyceryl group; $R^{17b}$ represents a linear, branched or cyclic, saturated or unsaturated hydrocarbon group which has from 5 to 22 carbon atoms and may be substituted with a hydroxyl or amino group, or the hydrocarbon group having, ester-bonded to the ω-terminal thereof, a linear or branched, saturated or unsaturated fatty acid which has from 8 to 22 carbon atoms and may be substituted with a hydroxy group; and $R^{18b}$ represents a hydrogen atom or an alkyl group which may be substituted with a hydroxy, hydroxyalkoxy, alkoxy, or acetoxy group and has from 1 to 8 carbon atoms in total].

$R^{17b}$ is preferably a nonyl group, a tridecyl group, a pentadecyl group, an undecyl group having linoleic acid ester-bonded to the ω-position thereof, a pentadecyl group having linoleic acid ester-bonded to the ω-position thereof, a pentadecyl group having 12-hydroxystearic acid ester-bonded to the ω-position thereof, and an undecyl group having methyl-branched isostearic acid amide-bonded to the ω-position thereof. The hydroxyalkoxy or alkoxy group as $R^{18b}$ has preferably from 1 to 8 carbon atoms.

As the pseudo type ceramides (L-2b), that having a hexadecyl group as $R^{14b}$, a hydrogen atom as $X^{1b}$, a pentadecyl group as $R^{17b}$, and a hydroxyethyl group as $R^{18b}$; that having a hexadecyl group as $R^{14b}$, a hydrogen atom as $X^{1b}$, a nonyl group as $R^{17b}$, and a hydroxyethyl group as $R^{18b}$; or that having a hexadecyl group as $R^{14b}$, a glyceryl group as $X^{1b}$, a tridecyl group as $R^{17b}$, and a 3-methoxypropyl group as $R^{18b}$ are preferred, with that of the formula (L-2b) having a hexadecyl group as $R^{14b}$, a hydrogen atom as $X^{1b}$, a pentadecyl group as $R^{17b}$, and a hydroxyethyl group as $R^{18b}$ being more preferred. Specific preferred examples include following ones:

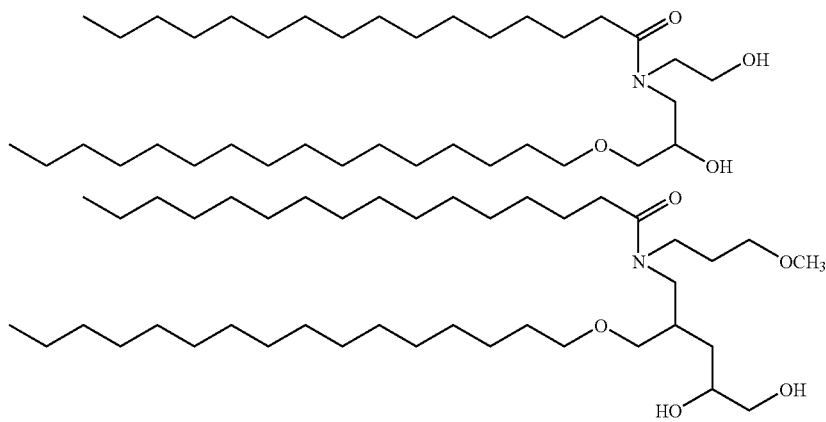

-continued

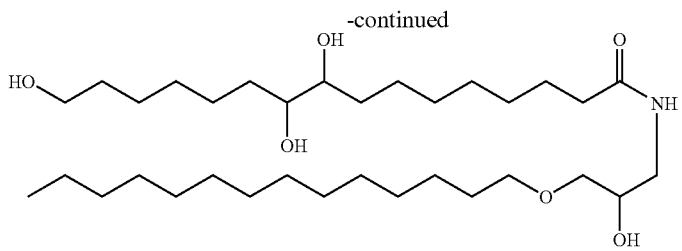

These amphipathic amide lipids may be used in combination of two or more thereof. The content of this component in the hair dye composition of the present invention is preferably from 0.01 to 10 mass %, more preferably from 0.05 to 5 mass % from the standpoint of the effect for recovering or preventing hair damage.

[(M): Amino Acid or Aminosulfonic Acid, or Derivative Thereof]

The hair dye composition of the present invention preferably contains an amino acid or an aminosulfonic acid, or a derivative thereof further as Component (M). Examples of the amino acid include neutral amino acids such as glycine, alanine, and proline, and basic amino acids such as lysine and arginine, and acidic amino acids such as glutamic acid and aspartic acid, while those of the aminosulfonic acid include taurine.

These amino acids and aminosulfonic acids, and derivatives thereof as Component (M) may be used in combination of two or more thereof. The content of this component in the hair dye composition of the present invention is preferably from 0.01 to 10 mass %, more preferably from 0.05 to 5 mass %, even more preferably from 0.1 to 3 mass % from the viewpoint of excellent effects for preventing hair damage and dyeing hair uniformly.

[(N): Polyhydric Alcohols]

The hair dye composition of the present invention preferably contains a polyhydric alcohol further as Component (N). Examples of the polyhydric alcohol include those having from 2 to 20 carbon atoms, more specifically, alkylene glycols such as ethylene glycol, diethylene glycol, triethylene glycol, polyethylene glycol, propylene glycol, dipropylene glycol, 1,2-butylene glycol, 1,3-butylene glycol, pentylene glycol, and hexylene glycol; glycerins such as glycerin, diglycerin, and polyglycerin; sugar alcohols such as xylitol, mannitol, galactitol, and sorbitol; and trimethylolethane, trimethylolpropane, and pentaerythritol.

These polyhydric alcohols as Component (N) may be used in combination of two or more thereof. The content of this component in the hair dye composition of the present invention is preferably from 0.1 to 20 mass %, more preferably from 0.5 to 15 mass %, even more preferably from 1 to 10 mass % from the standpoint of excellent effects for providing moisture to the hair and preventing excessive dryness of the hair.

[(O): Other Dyes]

The hair dye composition of the present invention may contain a direct dye further as Component (O) as a dye other than the oxidation dye as Component (C). Examples of the direct dye include nitro dyes, disperse dyes, basic dyes, and acid dyes. Examples of the nitro dye include 2-nitro-paraphenylenediamine, 2-amino-6-chloro-4-nitrophenol, 3-nitroparahydroxyethylaminophenol, 4-nitro-orthophenylenediamine, 4-amino-3-nitrophenol, 4-hydroxypropylamino-3-nitrophenol, HC Blue No. 2, HC Orange No. 1, HC Red No. 1, HC Yellow No. 2, HC Yellow No. 4, HC Yellow No. 5, HC Red No. 3, and N,N-bis-(2-hydroxyethyl)-2-nitro-paraphenylenediamine. Examples of the disperse dye include Disperse Violet No. 1, Disperse Blue No. 1, and Disperse Black No. 9; those of the basic dye include Basic Blue No. 99, Basic Brown No. 16, Basic Brown No. 17, Basic Red No. 76, Basic Red No. 51, Basic Yellow No. 57, Basic Yellow No. 87 and Basic Orange No. 31; and those of the acid dye include Orange No. 205 and Red No. 106.

These direct dyes as Component (O) may be used in combination of two or more thereof. The content of this component in the entire composition is preferably from 0.001 to 5 mass %, more preferably from 0.01 to 3 mass %.

[(P): Oxidizing Agent]

The hair dye composition of the present invention can further contain an oxidizing agent as Component (P). Examples of the oxidizing agent include hydrogen peroxide and hydrogen peroxide generators such as urea peroxide, melamine peroxide, sodium perborate, potassium perborate, sodium percarbonate, and potassium percarbonate. Of these, hydrogen peroxide is preferred. The content of the oxidizing agent as Component (P) in the hair dye composition of the present invention is, in terms of the amount of hydrogen peroxide, from 0.1 to 12 mass %, more preferably from 0.5 to 9 mass %, even more preferably from 1 to 6 mass % in view of sufficient hair dying effects and reduction in hair damage and scalp stimulation.

Alternatively, these oxidizing agents may be replaced with an oxidizing enzyme such as laccase and uricase.

[(Q): Persulfate]

The hair dye composition of the present invention can further contain a persulfate as Component (Q). Persulfates serve as a bleaching accelerator. Examples of the persulfate include ammonium persulfate, potassium persulfate, and sodium persulfate.

These persulfates as Component (Q) may be used in combination of two or more thereof. The content of this component in the hair dye composition of the present invention is preferably from 0.1 to 15 mass %, more preferably from 0.2 to 10 mass %, even more preferably from 0.5 to 5 mass % in view of sufficient bleaching effect and reduction in hair damage and scalp stimulation.

[Medium]

The hair dye composition of the present invention uses, as a medium therefor, water and, if necessary, an organic solvent. Examples of the organic solvent include lower alkanols such as ethanol and isopropanol, alkyl ethers of alkylene glycols such as diethylene glycol monoethyl ether, and aromatic alcohols such as benzyl alcohol and phenoxyethanol.

[Form of Composition]

The hair dye composition of the present invention is provided as a two-part hair dye having a first agent containing an alkali agent and an oxidation dye intermediate or a direct dye and a second agent containing an oxidizing agent; a three-part hair dye having, in addition to the first and second agents, a third agent containing a persulfate; a one-part hair dye containing an oxidation dye intermediate and an oxidizing enzyme; or a one-part hair dye containing an air oxidation dye.

[pH]

When the hair dye composition of the present invention is the above-described two-part or three-part composition, the first agent and the second agent of the hair dye composition of the present invention have preferably a pH from 8 to 12 and a pH from 2 to 5, respectively. When they are mixed, the pH is preferably from 9 to 11. When the hair dye composition is the one-part composition containing the oxidizing enzyme, it has a pH of preferably from 5 to 8 because optimum enzymatic activity is achieved within this pH range. When the hair dye composition is the one-part composition containing the air oxidation dye, it has a pH of preferably from 6 to 11, more preferably from 8 to 10.

[Others]

The hair dye composition of the present invention may contain, if necessary, other components to be used ordinarily for oxidative hair dye compositions. Examples of such optional components include fatty acids or salts thereof other than Component (A), animal or vegetable oils or fats, waxes, esters, ethers, nonionic surfactants other than Component (G), anionic surfactants, amphoteric surfactants, protein derivatives, pH regulators, thickeners, preservatives, chelating agents, stabilizers, antioxidants, plant extracts, crude-drug extracts, vitamin preparations, colorants, perfumes, and ultraviolet absorbers.

EXAMPLES

Examples 1 to 4 and Comparative Examples 1 to 3

The hair dye compositions having the compositions as shown in Table 1 were prepared in a conventional manner and they were evaluated for the below-described properties by a panel of five experts. Total scores are shown in Table 1.

(Uniformity of Dyeing)

The first agent and the second agent, each 1 g, were mixed thoroughly. The resulting mixture was applied to a gray-hair tress (1 g of Chinese hair) and a gray-hair tress (1 g of Chinese hair) damaged as a result of twice bleaching, respectively. After application, the tresses were left to stand for 20 minutes. They were then rinsed with running water, shampooed, and then dried. A difference in the dyeing uniformity between the tresses was visually evaluated based on the following five criteria, with Comparative Example 1 as a control.

+2: Superior in uniformity to Comparative Example 1

+1: A little superior in uniformity to Comparative Example 1

±0: Almost equal in uniformity to Comparative Example 1

−1: A little inferior in uniformity to Comparative Example 1

−2: Inferior in uniformity to Comparative Example 1

(Uniformity in Fading After Shampooing)

A dyed gray-hair tress (1 g of Chinese hair) and a gray-hair tress (1 g of Chinese hair) damaged as a result of twice bleaching were each subjected to a series of operations including shampooing and rinsing 20 times and then, dried. A difference in uniformity in color fading between the tresses was visually evaluated based on the following five criteria, with Comparative Example 1 as a control.

+2: Superior in uniformity to Comparative Example 1

+1: A little superior in uniformity to Comparative Example 1

±0: Almost equal in uniformity to Comparative Example 1

−1: A little inferior in uniformity to Comparative Example 1

−2: Inferior in uniformity to Comparative Example 1

(Smooth Finger Comparability After Shampooing and Rinsing)

The first agent and the second agent, each 10 g, were mixed thoroughly. The resulting mixture was applied to a black hair tress (10 g of Japanese hair) and the resulting tress was left to stand for 20 minutes. After the hair tress was rinsed with running water and shampooed, it was organoleptically evaluated based on the following five criteria, with Comparative Example 1 as a control:

+2: Superior in finger comparability to Comparative Example 1

+1: A little superior in finger comparability to Comparative Example 1

±0: Almost equal in finger comparability to Comparative Example 1

−1: A little inferior in finger comparability to Comparative Example 1

−2: Inferior in finger comparability to Comparative Example 1

(Smoothness After Drying)

The first agent and the second agent, each 10 g, were mixed thoroughly. The resulting mixture was applied to a black hair tress (10 g of Japanese hair) and the resulting tress was left to stand for 20 minutes. After the hair tress was rinsed with running water, shampooed, and dried, it was organoleptically evaluated based on the following five criteria, with Comparative Example 1 as a control.

+2: Superior in smoothness to Comparative Example 1

+1: A little superior in smoothness to Comparative Example 1

±0: Almost equal in smoothness to Comparative Example 1

−1: A little inferior in smoothness to Comparative Example 1

−2: Inferior in smoothness to Comparative Example 1

TABLE 1

|  |  | Examples | | | | Comp. Ex. | | |
| --- | --- | --- | --- | --- | --- | --- | --- | --- |
|  |  | 1 | 2 | 3 | 4 | 1 | 2 | 3 |
| First agent (wt. %) | Toluene-2,5-diamine | 0.5 | 0.5 | 0.5 | 0.5 | 0.5 | 0.5 | 0.5 |
|  | p-Aminophenol | 0.4 | 0.4 | 0.4 | 0.4 | 0.4 | 0.4 | 0.4 |
|  | m-Aminophenol | 0.4 | 0.4 | 0.4 | 0.4 | 0.4 | 0.4 | 0.4 |

TABLE 1-continued

|  |  | Examples | | | | Comp. Ex. | | |
| --- | --- | --- | --- | --- | --- | --- | --- | --- |
|  |  | 1 | 2 | 3 | 4 | 1 | 2 | 3 |
|  | Resorcin | 0.3 | 0.3 | 0.3 | 0.3 | 0.3 | 0.3 | 0.3 |
|  | 18-Methylicosanoic acid | 1.0 | — | 1.0 | — | — | 1.0 | — |
|  | 16-Methyloctadecanoic acid | — | 1.0 | — | 1.0 | — | — | — |
|  | Isostearic acid | — | — | — | — | 1.0 | — | — |
|  | Polyoxyethylene (2) cetyl ether | 0.3 | 0.3 | 0.3 | 0.3 | 0.3 | 0.3 | 0.3 |
|  | Polyoxyethylene (40) cetyl ether | 2.3 | 2.3 | 2.3 | 2.3 | 2.3 | 2.3 | 2.3 |
|  | Dimethyldiallylammonium chloride/acrylic acid copolymer (40 mass %, "Merquat 295", Nalco) | 1.5 | 1.5 | 1.5 | 1.5 | 1.5 | — | 1.5 |
|  | Behenyl alcohol | 1.2 | 1.2 | 1.2 | 1.2 | 1.2 | 1.2 | 1.2 |
|  | Stearyl alcohol | 5.5 | 5.5 | 5.5 | 5.5 | 5.5 | 5.5 | 5.5 |
|  | Propylene glycol | 5.0 | 5.0 | 5.0 | 5.0 | 5.0 | 5.0 | 5.0 |
|  | Tetrasodium edetate dihydrate | 0.1 | 0.1 | 0.1 | 0.1 | 0.1 | 0.1 | 0.1 |
|  | Anhydrous sodium sulfite | 0.3 | 0.3 | 0.3 | 0.3 | 0.3 | 0.3 | 0.3 |
|  | Ascorbic acid | 0.2 | 0.2 | 0.2 | 0.2 | 0.2 | 0.2 | 0.2 |
|  | Monoethanolamine | 1.0 | 1.0 | 1.0 | 1.0 | 1.0 | 1.0 | 1.0 |
|  | Strong ammonium hydroxide (28 wt. %) | 6.0 | 6.0 | 6.0 | 6.0 | 6.0 | 6.0 | 6.0 |
|  | Purified water | Balance | Balance | Balance | Balance | Balance | Balance | Balance |
| Second agent (wt. %) | 3-Octadecyloxypropyl-N,N,N-trimethylammonium chloride | 1.5 | 1.5 | — | — | — | — | — |
|  | Polyoxyethylene (13) cetyl ether | 2.0 | 2.0 | 2.0 | 2.0 | 2.0 | 2.0 | 2.0 |
|  | Cetyl alcohol | 3.5 | 3.5 | 3.5 | 3.5 | 3.5 | 3.5 | 3.5 |
|  | Stearyl alcohol | 1.8 | 1.8 | 1.8 | 1.8 | 1.8 | 1.8 | 1.8 |
|  | Liquid paraffin | 2.0 | 2.0 | 2.0 | 2.0 | 2.0 | 2.0 | 2.0 |
|  | Glycerin | 3.0 | 3.0 | 3.0 | 3.0 | 3.0 | 3.0 | 3.0 |
|  | Oxyquinoline sulfate | 0.1 | 0.1 | 0.1 | 0.1 | 0.1 | 0.1 | 0.1 |
|  | Phosphoric acid | Amount to adjust the second agent to pH 3.5 | | | | | | |
|  | Aqueous hydrogen peroxide (35 wt. %) | 16.0 | 16.0 | 16.0 | 16.0 | 16.0 | 16.0 | 16.0 |
|  | Purified water | Balance | Balance | Balance | Balance | Balance | Balance | Balance |
| Evaluation | Uniformity in dyeing power | +7 | +7 | +5 | +5 | — | −1 | −2 |
|  | Uniformity in fading after shampoo | +7 | +7 | +5 | +5 | — | −2 | −1 |
|  | Finger combability after shampooing and rinsing | +8 | +8 | +5 | +5 | — | −2 | −3 |
|  | Smoothness after drying | +8 | +8 | +5 | +5 | — | −2 | −4 |

Examples 5 to 7

Formulation Examples

Formulation examples of the hair dye composition of the present invention are shown in Table 2.

TABLE 2

|  |  | Examples | | |
| --- | --- | --- | --- | --- |
|  | First agent:second agent = 1:1 (mass ratio) | 5 | 6 | 7 |
| First agent (wt. %) | Toluene-2,5-diamine solution (20%) | 2.0 | 2.0 | 2.0 |
|  | Resorcin | 0.7 | 0.7 | 0.7 |
|  | meta-Aminophenol | 0.5 | 0.5 | 0.5 |
|  | para-Aminophenol | 0.5 | 0.5 | 0.5 |
|  | Propylene glycol | 7.0 | 7.4 | 7.4 |
|  | 18-Methylnonadecanoic acid | 1.0 | — | — |
|  | 18-Methylicosanoic acid | — | 1.0 | — |
|  | 16-Methyloctadecanoic acid | — | — | 1.0 |
|  | Dimethyldiallylammonium chloride/acrylic acid copolymer (40%, "Merquat 295", product of Nalco) | 2.5 | 2.5 | 2.5 |
|  | Polyoxyethylene (2) cetyl ether | 3.5 | 3.5 | 3.5 |
|  | Polyoxyethylene (40) cetyl ether | 3.0 | 3.0 | 3.0 |
|  | Cetyl alcohol | 4.0 | 4.0 | 4.0 |
|  | Stearyl alcohol | 4.0 | 4.0 | 4.0 |
|  | Anhydrous sodium sulfite | 0.5 | 0.5 | 0.5 |
|  | Ascorbic acid | 0.4 | 0.4 | 0.4 |
|  | Tetrasodium edetate dihydrate | 0.1 | 0.1 | 0.1 |
|  | Monoethanolamine | 2.0 | 2.0 | 2.0 |
|  | Strong ammonium hydroxide (28%) | 4.0 | 4.0 | 4.0 |
|  | Perfume | 0.4 | 0.4 | 0.4 |
|  | Purified water | Balance | Balance | Balance |
| Second agent (wt. %) | Aqueous hydrogen peroxide (35%) | 16.3 | 16.3 | 16.3 |
|  | Dialkyl (12-18)dimethylammonium chloride solution (75%, "QUARTAMIN D2345P", product of Kao) | 0.8 | 0.8 | 0.8 |

TABLE 2-continued

| First agent:second agent = 1:1 (mass ratio) | Examples | | |
|---|---|---|---|
| | 5 | 6 | 7 |
| Behenyltrimethylammonium chloride | 1.2 | 1.2 | 1.2 |
| 3-Octadecyloxypropyl-N,N,N-trimethylammonium chloride | 1.0 | 1.0 | 1.0 |
| Polyoxyethylene (20) cetyl ether | 7.0 | 7.0 | 7.0 |
| Cetyl alcohol | 5.0 | 5.0 | 5.0 |
| Stearyl alcohol | 2.0 | 2.0 | 2.0 |
| Propylene glycol | 4.0 | 4.0 | 4.0 |
| Oxyquinoline sulfate (2) | 0.05 | 0.05 | 0.05 |
| Etidronic acid | 0.05 | 0.05 | 0.05 |
| Sodium hydroxide | Amount to adjust the second agent to pH 3.5 | | |
| Purified water | Balance | Balance | Balance |

Example 8

Formulation Example 20

First Agent:Second Agent=1:1 (Mass Ratio)

| (First agent) | (mass %) |
|---|---|
| Paraphenylenediamine | 0.1 |
| Para-amino-ortho-cresol | 0.2 |
| Paraaminophenol | 0.35 |
| Metaaminophenol | 0.15 |
| 18-Methyloctanonanoic acid | 0.5 |
| 18-Methylicosanoic acid | 0.5 |
| Polyoxyethylene (2) stearyl ether | 3.0 |
| Polyoxyethylene (40) cetyl ether | 3.0 |
| Polydimethylallylammonium chloride*[1] | 1.0 |
| Amino-modified silicone | 0.5 |
| Highly polymerized dimethylpolysiloxane | 0.5 |
| Dimethylpolysiloxane oil | 1.0 |
| Cetyl alcohol | 6.0 |
| Stearyl alcohol | 1.0 |
| Coenzyme $Q_{10}$ solution*[2] | 0.05 |
| Diamide compound*[3] | 0.1 |
| L-arginine | 0.2 |
| Propylene glycol | 7.5 |
| Liquid paraffin | 1.0 |
| Anhydrous sodium sulfite | 0.5 |
| Ascorbic acid | 0.4 |
| Tetrasodium edetate dihydrate | 0.2 |
| Ammonium hydrogen carbonate | 1.0 |
| Monoethanolamine | 3.0 |
| Strong ammonium hydroxide | 3.0 |
| Perfume | 0.5 |
| Purified water | Balance |

*[1]"Merquat 100" (product of Nalco)
*[2]"Coenzyme $Q_{10}$" (product of Asahi Kasei Pharma)
*[3]Compound of the following formula

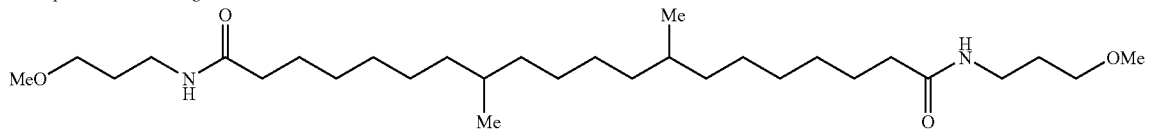

| (Second agent) | (mass %) | (Second agent) | (mass %) |
|---|---|---|---|
| Aqueous hydrogen peroxide (35%) | 16.3 | Glycine betaine | 0.5 |
| Propylene glycol | 4.0 | Cetyl alcohol | 7.0 |

-continued

| (Second agent) | (mass %) |
|---|---|
| 3-Octadecyloxypropyl-N,N,N-trimethylammonium chloride | 1.0 |
| Stearyltrimethylammonium chloride | 1.0 |
| Polyoxyethylene (20) cetyl ether | 7.0 |
| Oxyquinoline sulfate | 0.05 |
| Etidronic acid | 0.05 |
| Sodium hydroxide | Amount to adjust pH to 3.5 |
| Purified water | Balance |

Example 9

Formulation Example

| | (mass %) |
|---|---|
| 5,6-Dihydroxyindole | 0.3 |
| Amino-modified silicone emulsion*[4] | 0.5 |
| 16-Methyloctadecanoic acid | 0.2 |
| Dimethyldiallylammonium chloride/acrylic acid copolymer*[5] | 0.5 |
| Cetyltrimethylammonium chloride | 0.1 |
| Polyoxyethylene (9) tridecyl ether*[6] | 1.6 |
| 1,3-Butylene glycol | 3.0 |
| 95 vol % Ethanol | 6.0 |
| Hydroxypropyl xanthan gum | 0.7 |
| Ascorbic acid | 0.3 |
| Monoethanolamine | 0.5 |
| Sodium hydroxide | Amount to adjust pH to 10 |

-continued

| | (mass %) |
|---|---|
| Perfume | 0.3 |
| Purified water | Balance |

*[4]"Silicone SM8704C" (product of Dow Corning Toray)
*[5]"Merquat 280 (product of Nalco)
*[6]"SOFTANOL 90" (product of Nippon Shokubai)

The invention claimed is:

1. An oxidative hair dye composition comprising the following Components (A) to (D):
(A) an iso-fatty acid or an anteiso-fatty acid having from 19 to 30 carbon atoms, or a salt thereof;
(B) a polymer or a copolymer of a diallyl quaternary ammonium salt;
(C) an oxidation dye; and
(D) an alkali agent.

2. The oxidative hair dye composition according to claim 1, further comprising the following Component (E):
(E) a silicone.

3. The oxidative hair dye composition according to claim 1 or 2, further comprising the following Component (F):
(F) a cationic surfactant.

4. The oxidative hair dye composition according to claim 1, further comprising the following Component (G):
(G) a polyoxyethylene alkyl ether type nonionic surfactant.

5. The oxidative hair dye composition according to claim 2, further comprising the following Component (G):
(G) a polyoxyethylene alkyl ether type nonionic surfactant.

6. The oxidative hair dye composition according to claim 3, further comprising the following Component (G):
(G) a polyoxyethylene alkyl ether type nonionic surfactant.

* * * * *